United States Patent
Strömmer

(10) Patent No.: US 7,145,985 B2
(45) Date of Patent: Dec. 5, 2006

(54) SENSOR ARRANGEMENT AND METHOD FOR DIGITAL SCANNING IMAGING

(75) Inventor: Pekka Strömmer, Espoo (FI)

(73) Assignee: Planmed Oy, Helsinki (FI)

( * ) Notice: Subject to any disclaimer, the term of this patent is extended or adjusted under 35 U.S.C. 154(b) by 10 days.

(21) Appl. No.: 10/496,228

(22) PCT Filed: Nov. 22, 2002

(86) PCT No.: PCT/FI02/00945

§ 371 (c)(1),
(2), (4) Date: Aug. 27, 2004

(87) PCT Pub. No.: WO03/044564

PCT Pub. Date: May 30, 2003

(65) Prior Publication Data

US 2004/0267488 A1 Dec. 30, 2004

(30) Foreign Application Priority Data

Nov. 23, 2001 (FI) ................................. 20012301

(51) Int. Cl.
*H05G 1/64* (2006.01)

(52) U.S. Cl. ................. 378/98.8; 250/370.09

(58) Field of Classification Search ............... 378/98.8, 378/37; 250/370.09, 370.11
See application file for complete search history.

(56) References Cited

U.S. PATENT DOCUMENTS 3,790,785 A * 2/1974 Paolini et al. ......... 250/363.01
5,508,507 A * 4/1996 Nelson et al. ......... 250/214 LA
5,963,879 A    10/1999 Woodward et al.

FOREIGN PATENT DOCUMENTS

WO    WO 95/27369    10/1995
WO    WO 00/53093     9/2000

* cited by examiner

*Primary Examiner*—Courtney Thomas
*Assistant Examiner*—Chih-Cheng Glen Kao
(74) *Attorney, Agent, or Firm*—Hamilton, Brook, Smith & Reynolds, P.C.

(57) ABSTRACT

The invention relates to digital scanning imaging by electromagnetic radiation. To reduce the difference between the resolutions in, the scanning direction and the direction perpendicular thereto, pixels (P1, P2, P3, P4, P5, P6) in the scanning direction are connected to counters (C1, C2, C3) through switching means (Sm1, Sm2, Sm3) which allow pulses to be directed to the counter of a neighboring pixel, in addition to its own pixel, for counting, whereby the reading area can be divided into a plurality of "partial pixels" and by suitably changing the switch positions, it is possible to follow the imaging scan as reading areas formed by the "partial pixels".

16 Claims, 2 Drawing Sheets

SENSOR ARRANGEMENT AND METHOD FOR DIGITAL SCANNING IMAGING

RELATED APPLICATIONS

This application is the U.S. National Stage of International Application No. PCT/FI02/00945, filed Nov. 22, 2002, published in English, and claims priority under 35 U.S.C. § 119 or 365 to Finnish Application No. 20012301, filed Nov. 23, 2001.

FIELD OF THE INVENTION

The invention relates to digital imaging of an object implemented by electromagenetic radiation, in particular to scanning imaging by TDI (Time Delay Integration) method using x-rays.

BACKGROUND OF THE INVENTION

Imaging based on electromagnetic radiation can be implemented, for instance, as so-called full-field imaging or scanning imaging with a narrow sensor. As the manufacturing costs of digital sensors, with current technology, grow exponentially as a function of sensor area, there is a tendency to employ scanning imaging whenever possible. In scanning imaging the area to be imaged is scanned with a narrow fan-beam, typically with a beam considerably narrower than the object to be imaged, and the scanning movement of the beam is followed by a narrow sensor from which image information is continuously read out during the imaging scan.

Semiconductor sensors commonly used in digital imaging have a basic structure in which small picture elements, i.e. pixels, form larger radiation-sensitive areas. Sensors of traditional technology are able to detect mainly wavelengths of visible light only, which means that x-ray quanta, for example, must be converted to light photons which are in turn converted into electric signal that forms the image information of the pixels. In x-ray sensors of more modern technology, the so-called direct detection sensors, the radiation arriving in the area of picture elements is absorbed in a medium in which it is directly converted into electron-hole pairs, in other words, into electrically detectable charges. The medium can be biased (photoelectric) semiconductor material, such as Ge, Si, Se, GaAs, Hgl, CdTe, CdZnTe or Pbl, and when an electric field is arranged over it, each of the electron-hole pairs produced by radiation quanta can be collected within the area of its own pixel. Such a sensor, utilizing collimation by an electric field and direct detection, enables very high quantum efficiency (dqe) without sacrificing resolution, as the material layer detecting radiation can be arranged sufficiently thick so as to absorb all the radiation quanta that enter it, without the charge generated thereby spreading to the area of adjacent pixels. Electric information of a pixel electrode can be detected either by measuring the amount of charge accumulated into a pixel in a time unit or, by counting each quantum absorbed into a pixel area discretely, i.e. using e.g. technology disclosed in WO 98/16853, according to which each charge impulse generated upon absorption of a radiation quantum increments a counter. When this detection method based on so-called photon counting is used, each of the quanta of different energy levels are counted individually, instead of first accumulating the charge generated thereby and subsequently measuring the magnitude of the accumulated charge. Using the photon counting method, the contrast of an image produced is remarkably improved.

Typically, pixels of the digital sensors have equal vertical and horizontal dimensions, the pixels being arranged such that they are evenly distributed on the active area of the sensor. When scanning imaging is implemented by transferring image information from one pixel to another as pixel-sized units, the point being imaged on each pixel "swings" in the scanning direction as a function of the effective pixel size used. In these typical prior art sensors, resolution in scanning imaging is clearly poorer in the scanning direction than in the direction perpendicular to it. In practice it has been found to be about half of the perpendicular resolution.

A seemingly natural solution to improve resolution in scanning direction would be reduction of pixel size, for instance, halving the size. However, that would quadruple the amount of read-out electronics required for the sensor and the amount of image information produced. Also, even though resolution in the scanning direction could be improved in this manner to the desired level, resolution in the perpendicular direction would still be twice better than in the scanning direction.

In principle, the pixel arrangement could be implemented densified closer only in the scanning direction, in other words, by reducing dimension of the pixels only in the scanning direction, but also in this case the amount of read-out electronics and the amount of image information would be increased respectively.

BRIEF DESCRIPTION OF THE INVENTION

The object of the invention is to provide such a sensor arrangement and a method for scanned digital imaging that will provide new possibilities to image an object with higher resolution in the scanning direction than in prior art with respect to that in the perpendicular direction, yet not increasing the amount of image information nor at least substantially that of the read-out electronics. This is achieved with a sensor arrangement and a method the characterizing features of which being defined in the attached independent claims. In the attached dependent claims, in turn, some preferred embodiments of the invention are defined.

The invention is based on an idea by which it is possible to reduce the difference in resolution between the scanning direction and the direction perpendicular thereto in a novel and advantageous manner in view of the amount of read-out electronics required. When pixels may be connected, according to prior art, to counters counting electric impulses received from the pixels, in accordance with the invention they are not necessarily connected to the counters directly but, at least in part, through switching means which permit directing of impulses not only to their "own" counters but also to counters of adjacent pixels The reading area can thus be divided into a plurality of "partial pixels" to form reading areas, which may then be arranged to follow the imaging scan by properly altering the switch connections. In this manner, for instance, reducing the pixel size to half in the scanning direction does not considerably increase the total amount of read-out electronics, however, as the amount of counting electronics remains the same. Naturally, to enable scanning imaging, in all cases the counters must also be arranged such that they are loaded in the scanning direction from the counters of previous columns, as taught in the Applicant's Finnish patent application FI 2000 0592, for instance.

BRIEF DESCRIPTION OF THE DRAWINGS

In the following, the invention will be described in connection with preferred embodiments, with reference to the attached drawings, wherein.

DETAILED DESCRIPTION OF THE INVENTION

In the following the invention will be described using as an example x-rays and sensor technology and arrangement disclosed in the Finnish patent application FI 2000 0592, without limiting the invention to these solutions, however. Patent application FI 2000 0592 is incorporated herein as reference. The basic idea of the invention can be applied to any scanning imaging which utilizes electromagnetic radiation and in which image information is read as pulses countable with a counter, in particular to x-ray sensors based on direct detection.

Figure 1:
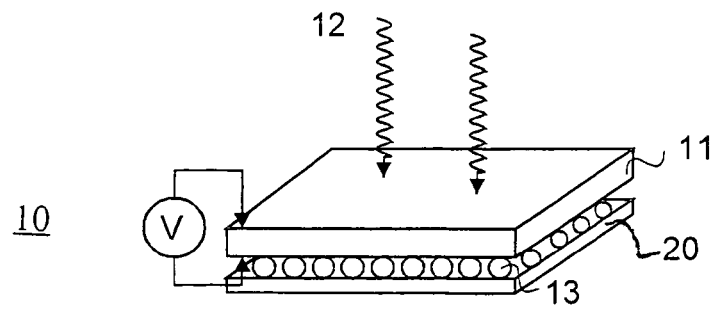
FIG. 1 illustrates the structure of a sensor based on direct detection of x-rays.

FIG. 1 shows a basic structure of one typical sensor 10 based on direct detection of x-rays, in which a means 11 absorbing radiation 12 is a material layer having an area X*Y, which converts the radiation directly into an electric signal. The material layer is placed in a strong electric field V. The radiation converting layer may consist, for instance, of a relatively thin (semiconductor) material layer (Ge, Si, Se, GaAs, Hgl, CdTe, CdZnTe, Pbl), whose surface opposite to the surface facing radiation 12, and thus not visible in FIG. 1, is provided with pixel electrodes that cover the surface in a desired manner. By means of the electric field, the signal generated can thus be collimated on pixel level and detected, for instance, by read-out electronics 20 comprising a substrate whose area is substantially equal to that of the semiconductor-based absorption means 11 and e.g. an indium ball joint 13 associated with each pixel electrode. The reading electronics may be implemented by CMOS (Complementary Metal-Oxide Semiconductor) technology, for instance.

Figure 2:
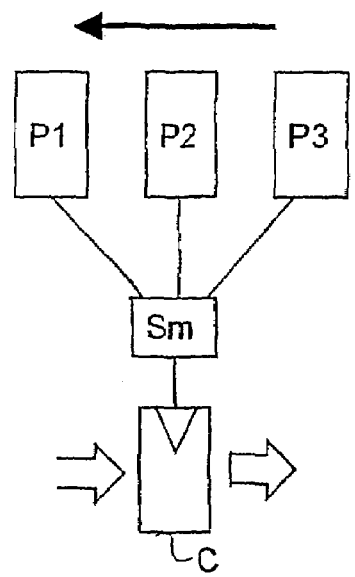
FIGS. 2 and 3 are block diagrams illustrating the principle of the invention.
Figure 3:
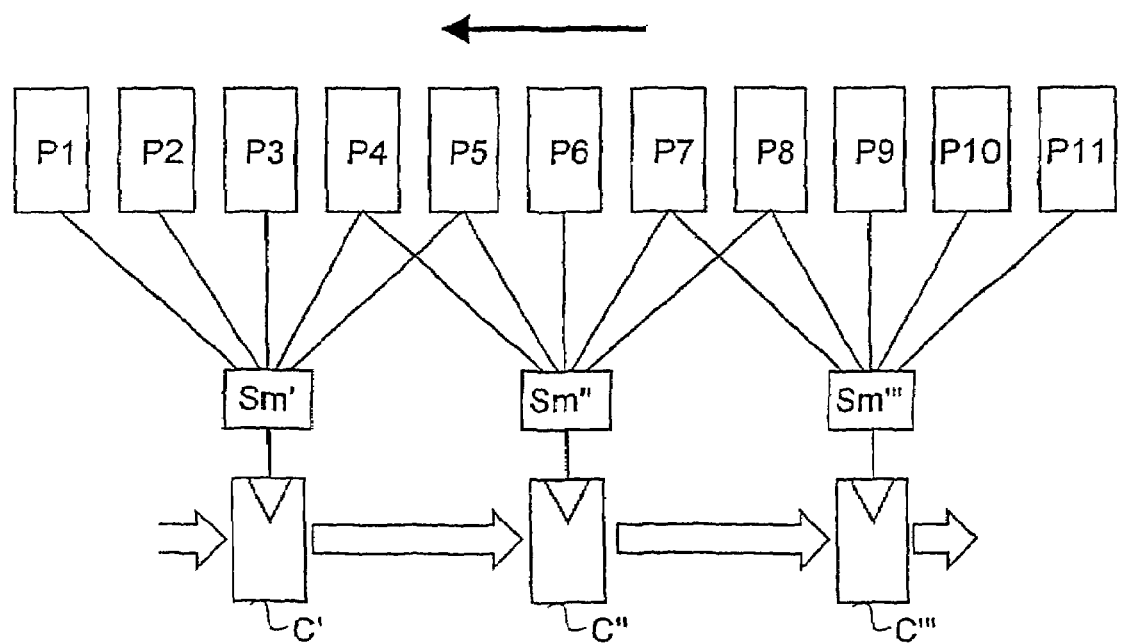

In FIGS. 2 and 3 the principle of the invention is shown by means of simplified block diagrams. In the embodiments according to the Figures the read-out electronics may be implemented, for instance, by arranging a specific connector surface for each pixel electrode P1, P2, . . . and by interconnecting the counters C, C', C", C'" in the direction of the scanning movement (thin arrow in the figures) such that each counter C, C', C", C'" may be loaded in parallel (broad arrow in the figures) from the counter of the pixel on the same line in the previous pixel column. The counters of the first column may be arranged to load to zero, whereby the sensor signals will be readily reset to zero.

FIG. 2 shows a first arrangement according to the invention, which comprises the most relevant elements of the minimum assembly of the invention for one counter C. In the arrangement of FIG. 2, pixel electrodes P1, P2, P3 are not connected to the counter C directly but a switching means Sm has been arranged between them. The three pixel electrodes P1, P2, P3 are connectable to the switching means Sm in the scanning direction, which makes it possible to select the two of the pixel electrodes P1, P2, P3 from which pulses will be directed to the counter C at each (specific) instant of time. In the arrangement of FIG. 2, the size of the reading area is two pixel electrodes, and the switching means is used to direct pulses to the counter C first from the reading area consisting of the pixel electrodes P1 and P2, and then from the reading area consisting of the pixel electrodes P2 and P3. During imaging the scanning movement is thus followed on the sensor in units of two adjacent pixel electrodes by means of the switching means Sm with steps of one pixel electrode length, for example, in other words, at each instant of time pulses are directed to the counter C from the reading area consisting of two adjacent pixel electrodes.

FIG. 3 illustrates a second arrangement according to the invention on one pixel electrode/counter line. In the example of FIG. 3, it is possible to connect five pixel electrodes to each counter C', C", C'" through a switching means Sm', Sm", Sm'" such that four of the pixel electrodes are also connectable to another switching means. For instance, the pixel electrodes P4 and P5 of the pixel electrodes P4, P5, P6 and P7, connectable to the counter C" through the switching means Sm", are also connectable to the counter C' through the switch Sm', and the pixel electrodes P7 and P8 are also connectable to the counter C'" through the switch Sm'".

Generally speaking, when applied to a sensor structure as described above, the arrangement of the invention consists of a structure, in which—when N is 2 or a higher integer indicating the size of the reading area, or in fact, that of the pixel—each set of 2N−1 successive pixel electrodes is connectable to one switching means Sm such that the midmost pixel electrode P is connectable only to said one switching means Sm, and the pixel electrodes preceding the midmost one in the scanning direction are also connectable to a switching means Sm preceding said switching means Sm and the subsequent pixel electrodes P in the scanning direction also to a switching means subsequent to said switching means Sm. As the scanning proceeds, the reading area is shifted by changing the switch positions for one pixel electrode P at a time (at least) such that, during each integration period, image information is read from each pixel electrode P only to one counter C. The counters C are loaded from the preceding counters at the same time when the reading area is transferred to the subsequent counter, in other words, when moving with steps of one pixel electrode, every time when said midmost pixel electrode P has been the last pixel electrode of the reading area.

In the example illustrated in FIG. 3, the width of the reading area in the scanning direction is thus three pixel electrodes P wide, whereby the switching means Sm directs to each of the counters C three out of the possible five pulses of the pixel electrodes and as the scanning movement proceeds, shift the edge of the reading area from one pixel electrode to the next in the direction opposite to the scanning direction. Loading counters from preceding counters takes place in the same direction as shifting the reading area, naturally.

In the above-described pixel arrangement, when the pixel dimension in the scanning direction is arranged to be about half of that in the perpendicular direction, an arrangement is provided by which resolution is approximately the same in both directions.

Figure 4:
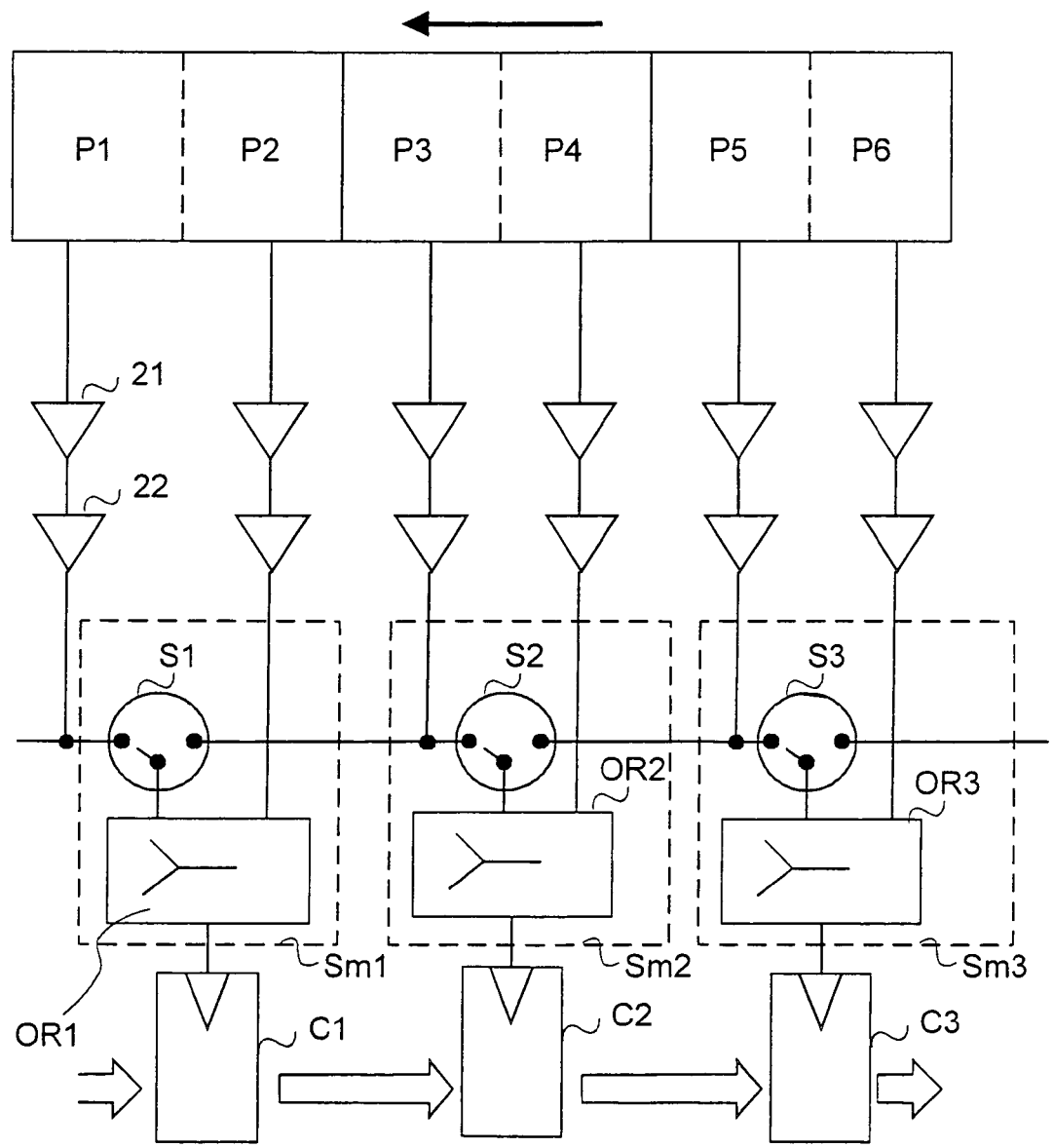
FIG. 4 illustrates electronics arrangement according to one preferred embodiment of the invention.

FIG. 4 shows a more detailed block diagram of a sensor arrangement corresponding to the embodiment of the invention in FIG. 2. The electronics arrangement according to this embodiment comprises pixel electrodes P1, P2, P3, P4, P5 and P6 in the scanning direction, each of them comprising a signal preamplifier 21 and a comparator 22. Operation of the comparator is based on the idea that, in accordance with optional, externally set comparison level, it either detects or does not detect a quantum absorbed in the area of the pixel electrode P. The comparison level is the energy level to which the energy of a received pulse is compared, and typically the pulse is counted if its energy exceeds the comparison level. In some embodiments of the invention it is also possible to count pulses whose energy is below a comparison level. The use of the comparator 22 is no requirement for the application of the invention in practice. In embodiments without a comparator 22 the counter C simply counts all the pulses coming from the pixel electrodes.

The switching means Sm1, Sm2, Sm3 may be implemented by circuit means OR1, OR2, OR3 connecting the switches S1, S2, S3 and the pulse sequences as shown in FIG. 4. The switches S1, S2, S3 are controlled with clock signals, for instance, as a function of scanning velocity and pixel size, in a manner that is obvious to a person skilled in the art in accordance with the specific imaging conditions of scanning imaging. The circuit means OR connecting the pulse sequences is an OR gate, which combines the pulses received from different pixel electrodes P such that the pulses of different pulse sequences are directed to the counter C as one pulse sequence.

In practice, the arrangement of FIG. 4 is controlled such that first the counter C1, for instance, counts pulses of the pixel electrodes P1 and P2 and then pulses of the pixel electrodes P2 and P3, the contents of the counter C1 is transferred to counter C2 and counting is continued in a corresponding manner by counting first pulses of the pixel electrodes P3 and P4 and then pulses of the pixel electrodes P4 and P5, etc.

In the solution of FIG. 4, the counters C1, C2, C3 may be, for instance, pixel-specific 12- to 16-bit digital counters that count each voltage or current pulse whose energy level exceeds the comparison level. These counters can be provided with a circuit which prevents counting when the counter is full, whereby overexposure does not cause any fault in the image other than the fact that the pixel signal to be measured is at its maximum value. In addition, as stated above, the counters for enabling scanning imaging are arranged to be loadable from the preceding counters in the opposite direction to the scanning direction and the contents of the counters is read out at the trailing edge of the sensor in the scanning direction by any technique known per se. The contents may be read out as such in parallel, or in order to minimize the number of signal conductors, they may be loaded in parallel into a shift register and transferred from the sensor in serial format using one conductor.

The way the results of the counters are read out and loaded into a shift register, for instance, is not a relevant aspect of the invention, however. Further, the invention can be applied regardless of whether the image information is detected on the basis of all the quanta detected in the area of pixels during imaging or by counting the number of detected quanta exceeding a threshold level, which level may be selectable.

The sensor arrangement and method of the invention enable use of subsequent image processing techniques known per se. For instance, if implementation of the invention leads to excessive resolution in some imaging applications, it is possible to combine the signals detected by the counters into larger entities, for instance, in an image processing computer so as to optimise the radiation dose/imaging resolution according to the requirements of the object in question.

It is apparent to a person skilled in the art that as technology advances, the basic idea of the invention can be implemented in a variety of ways. In particular, the invention is applicable to mammography utilizing scanning technique, as in mammography high resolution is typically required. Hence, the invention and its embodiments are not restricted to the above-described examples, but they may vary within the scope of the attached claims.

The invention claimed is:

1. A sensor arrangement for a sensor in digital scanning imaging utilizing electromagnetic radiation, the arrangement comprising
   a radiation absorbing element which includes or to which is integrated material converting radiation quanta into electron-hole pairs,
   pixel electrodes (P1, P2, P3) on a surface opposite to a radiation-receiving surface of said element for dividing the element into pixels,
   counters (C) which are connected to said pixel electrodes (P1, P2, P3) for counting pulses received therefrom,
   counter-specific switching means (Sm) that are arranged between the counters (C) and the pixel electrodes (P1, P2, P3) such that
   in a scanning direction of the sensor, successive structures are obtained, where one counter (C) and one switching means (Sm) are arranged for every N successive pixel electrodes (P1, P2, P3), N being an integer whose value is at least two,
   to which switching means (Sm) are connected sets of pixel electrodes (P1, P2, P3) consisting of 2N−1 successive pixel electrodes (P) such that of each set
   the midmost pixel electrode (P2) is connected to only one switching means (Sm),
   the pixel electrodes (P1) preceding said midmost pixel electrode (P2) are arranged connectable to both said one switching means and one preceding switching means (Sm), and
   pixel electrodes (P3) subsequent to said midmost pixel electrode (P2) are arranged connectable to both said one switching means and one subsequent switching means (Sm).

2. A sensor arrangement as claimed in claim 1, wherein a dimension of pixels produced by the pixel electrodes (P1, P2, P3) in the scanning direction is arranged to be about half of that in their perpendicular direction.

3. A sensor arrangement as claimed in claim 1 wherein the switching means (Sm) are arranged to direct pulses to counters (C) from reading areas, which consist of N successive pixel electrodes (P1, P2, P3) such that as a scanning movement proceeds the switching means (Sm) shift the reading areas in the opposite direction to the scanning direction for one pixel electrode (P1, P2, P3) at a time.

4. A sensor arrangement as claimed in claim 1, wherein means are arranged therein for loading the counters (C) from the preceding counters every time reading areas consisting of N successive pixel electrodes (P1, P2, P3) are transferred to subsequent counters.

5. A sensor arrangement as claimed in claim 1, wherein the switching means (Sm) are controlled by a clock signal taking into account velocity of movement in the scanning direction and pixel size.

6. A sensor arrangement as claimed in claim 1, wherein the electronics arrangement thereof comprises preamplifiers (21).

7. A sensor arrangement as claimed in claim 6, wherein the electronics arrangement thereof also comprises comparators (22).

8. A sensor arrangement as claimed in claim 1, wherein said switching means (Sm1, Sm2, Sm3) comprise a switch (S1, S2, S3) for selecting said selectable preceding and subsequent pixel electrodes (P1, P2, P3; P4, P5, P6) and a circuit means (OR1, OR2, OR3) for combining pulse sequences coming from different pixel electrodes (P1, P2, P3, P4, P5, P6) prior to directing a signal to the counters (C1, C2, C3).

9. A method in digital scanning imaging utilizing electromagnetic radiation, comprising at least:
   scanning over an object to be imaged with a beam narrower than the object;
   following the beam behind the object with a sensor arrangement comprising a plurality of pixels, in which absorbed radiation quanta are detected as pulses generated on a pixel and in which said pulses are counted by counters connected to the pixels;
   directing pulses from the pixels to the counters through counter-specific switching means from a reading area that is at least two pixels wide and as scanning proceeds, the reading area is shifted at least once during a time when pulses are directed to one counter, such that in connection with every shift of the reading area, pulses from at least one of the pixels that belonged to said reading area will begin to be directed to a counter that is other than the one counter used before the shift.

10. A method as claimed in claim 9, wherein pulses are directed, at least in two phases, through the switching means to one counter from a set of pixels consisting of 2N−1 successive pixels, the N being an integer which indicates a width of the reading area and whose value is at least two, said successive pixels being connected to the switching means such that the midmost pixel of said set is connected to only one of said switching means, the pixels preceding said midmost pixel being connected to either said one switching means or the one preceding said one switching means and the pixels subsequent to said midmost pixel being connected to either said one switching means or the one subsequent to said one switching means in a way that pulses are always directed to each counter from N pixels.

11. A method as claimed in claim 9 wherein reading areas consisting of N pixels, as the scanning movement proceeds, are shifted in the opposite direction to the scanning movement for one pixel at a time by means of said switching means.

12. A method as claimed in claim 9, further comprising a step of loading a counter onto a subsequent counter in connection with the reading area shift from one counter to a subsequent counter.

13. A method as claimed in claim 9 wherein pulse sequences from different pixels which are to be directed to the same counter, are directed to said same counter through a circuit means, which combines said pulse sequences.

14. A method as claimed in claim 9 further comprising the step of controlling said switching means to shift reading areas by a clock signal, which takes into account velocity of movement in the scanning direction and pixel size.

15. A method as claimed in claim 9, further comprising the step of counting pulses from pixels whose dimension in the scanning direction is smaller than their dimension perpendicular thereto.

16. A sensor arrangement for a sensor in digital scanning imaging utilizing electromagnetic radiation, the arrangement comprising
   a radiation absorbing element which includes or to which is integrated material converting radiation quanta into electron-hole pairs, the element divided into pixels,
   counters (C), which are connected to said pixels, and arranged for counting pulses received therefrom,
   counter-specific switching means (Sm) that are arranged between the counters (C) and the pixels such that
   in a scanning direction of the sensor, successive structures are obtained, where one counter (C) and one switching means (Sm) are arranged for every N successive pixels, N being an integer whose value is at least two,
   to which switching means (Sm) are connected sets of pixels consisting of 2N−1 successive pixels in such a way that of each set
   the midmost pixel is connected to only one switching means (Sm),
   the pixels preceding said midmost pixel are arranged connectable to both said one switching means and one preceding switching means (Sm), and
   pixels subsequent to said midmost pixel are arranged connectable to both said one switching means and one subsequent switching means (Sm).

* * * * *